US012277267B2

(12) United States Patent
Silva et al.

(10) Patent No.: US 12,277,267 B2
(45) Date of Patent: Apr. 15, 2025

(54) TWO-WAY COMMUNICATION BETWEEN HEAD-MOUNTED DISPLAY AND ELECTROANATOMIC SYSTEM

(71) Applicant: SentiAR, Inc., St. Louis, MO (US)

(72) Inventors: Jennifer N. Avari Silva, St. Louis, MO (US); Jonathan R. Silva, St. Louis, MO (US); Michael K. Southworth, St. Louis, MO (US); Ignacio Soriano, Madrid (ES); Matthew Dagley, Chicago, IL (US); Christopher Michael Andrews, Chesterfield, MO (US); Sharif Razzaque, St. Louis, MO (US); Irene Hougard, St. Louis, MO (US); Berk Tas, Eden Prairie, MN (US)

(73) Assignee: SentiAR, Inc., St. Louis, MO (US)

( * ) Notice: Subject to any disclaimer, the term of this patent is extended or adjusted under 35 U.S.C. 154(b) by 0 days.

(21) Appl. No.: 18/305,121

(22) Filed: Apr. 21, 2023

(65) Prior Publication Data

US 2023/0341932 A1     Oct. 26, 2023

Related U.S. Application Data

(60) Provisional application No. 63/333,900, filed on Apr. 22, 2022.

(51) Int. Cl.
| | |
|---|---|
| *G06F 3/01* | (2006.01) |
| *G06F 3/04815* | (2022.01) |
| *G06F 3/14* | (2006.01) |
| *G06T 19/00* | (2011.01) |

(52) U.S. Cl.
CPC .......... *G06F 3/013* (2013.01); *G06F 3/04815* (2013.01); *G06F 3/1423* (2013.01); *G06T 19/006* (2013.01); *G06T 2200/24* (2013.01)

(58) Field of Classification Search
CPC .... G06F 3/013; G06F 3/04815; G06F 3/1423; G06T 19/006; G06T 2200/24
See application file for complete search history.

(56) References Cited

U.S. PATENT DOCUMENTS

| | | | |
|---|---|---|---|
| 10,438,415 B2 * | 10/2019 | Hendricks | G09B 5/02 |
| 12,001,602 B2 * | 6/2024 | Alcaide | G06F 3/04842 |
| 2016/0026242 A1 | 1/2016 | Burns et al. | |
| 2018/0200018 A1 | 7/2018 | Silva et al. | |
| 2018/0293802 A1 | 10/2018 | Hendricks et al. | |
| 2020/0268296 A1 * | 8/2020 | Alcaide | G06F 3/017 |
| 2020/0272231 A1 | 8/2020 | Klein et al. | |

OTHER PUBLICATIONS

PCT International Search Report and Written Opinion, PCT Application No. PCT/US2023/66070, Jul. 21, 2023, 8 pages.

* cited by examiner

*Primary Examiner* — Peter D McLoone
(74) *Attorney, Agent, or Firm* — Fenwick & West LLP

(57) ABSTRACT

A processing system provides two-way communication between an electroanatomic navigation and mapping system (EAMS) and a head-mounted display (HMD). A user wearing the HMD can use hands-free or touch-free actions to interact with a user interface for EAMS information displayed by the HMD (e.g., 3D augmented reality graphics) or by a display monitor (e.g., 2D graphics). For example, the processing system updates the position of a cursor on the display monitor to track a gaze direction of the user as determined by the HMD.

20 Claims, 3 Drawing Sheets

200

```
┌─────────────────────────────────────────┐
│ Provide image data for display by a HMD │
│ worn by a user based on data provided   │
│ to a display monitor for a              │
│ user interface                          │
│ 210                                     │
└─────────────────────────────────────────┘
                    ↓
┌─────────────────────────────────────────┐
│ Receive a gaze direction of the user    │
│ 220                                     │
└─────────────────────────────────────────┘
                    ↓
┌─────────────────────────────────────────┐
│ Determine a position of a cursor        │
│ displayed on the user interface based   │
│ on the gaze direction                   │
│ 230                                     │
└─────────────────────────────────────────┘
                    ↓
┌─────────────────────────────────────────┐
│ Provide the position of the cursor to   │
│ the display monitor                     │
│ 240                                     │
└─────────────────────────────────────────┘
                    ↓
┌─────────────────────────────────────────┐
│ Receive a user input from the HMD       │
│ responsive to an action performed by    │
│ the user                                │
│ 250                                     │
└─────────────────────────────────────────┘
                    ↓
┌─────────────────────────────────────────┐
│ Provide user input information to the   │
│ display monitor to update the user      │
│ interface based on the user input and   │
│ the position of the cursor              │
│ 260                                     │
└─────────────────────────────────────────┘
```

FIG. 2

TWO-WAY COMMUNICATION BETWEEN HEAD-MOUNTED DISPLAY AND ELECTROANATOMIC SYSTEM

CROSS REFERENCE TO RELATED APPLICATION

This application claims the benefit of priority to U.S. Provisional Application No. 63/333,900, filed on Apr. 22, 2022, which is incorporated herein by reference in its entirety for all purposes.

TECHNICAL FIELD

This disclosure generally relates to systems for electroanatomic mapping and manipulation of displays in a virtual, augmented, or mixed reality environment.

BACKGROUND

An electroanatomic navigation and mapping system (EAMS) aids physicians in performing minimally-invasive medical procedures. The EAMS tracks the distal ends of medical tools such as catheters. The EAMS displays positions of the medical tools, in relationship to the patient anatomy and other patient data, via real-time computer-generated images displayed on a (monoscopic) 2D computer screen (e.g., LCD flat panel mounted on a boom above the patient).

Conventionally, a user operates the EAMS using a keyboard and mouse. Generally, the hands of a physician performing a medical procedure are sterile and occupied by the task of holding and manipulating medical tools. Thus, the physician cannot directly interact with the EAMS. Instead, another person (e.g., a technician) operates the EAMS on behalf of the physician. The physician conveys requests to the EAMS technician via voice.

BRIEF DESCRIPTION OF DRAWINGS

The disclosed embodiments have advantages and features which will be more readily apparent from the detailed description, the appended claims, and the accompanying figures (or drawings). A brief introduction of the figures is below.

FIG. 2 is a flowchart of a process for user control in an augmented reality environment according to an embodiment.

SUMMARY

Figure 1:
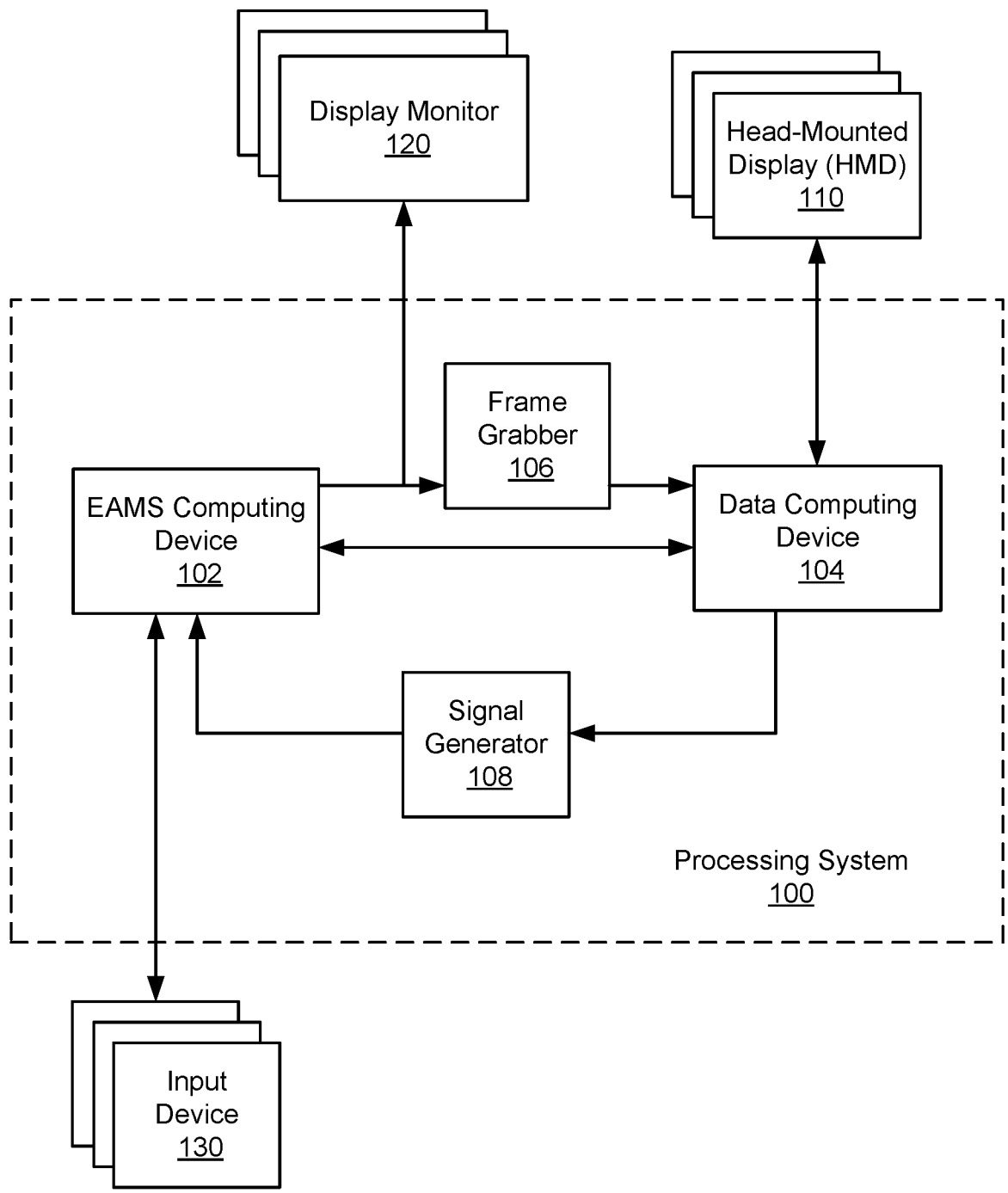
FIG. 1 illustrates an example system environment for a processing system according to an embodiment.

There are benefits to supplementing or connecting the EAMS with a head-mounted display (HMD) worn by a user that tracks the position and orientation of the user's head and/or eyes/pupils, such as the Sentiar™ SentEP. The EAMS sends data about the patient anatomy and about the positions and statuses of the tracked catheters or other medical tools. The HMD generates 3D imagery of this data from the EAMS, and displays the 3D imagery to the physician. The user can rotate or otherwise change their view of the EAMS data by simply moving their head, instead of having to verbally ask an EAMS technician to manipulate the view with a mouse or keyboard. Furthermore, the HMD can also present a user-interface (e.g., menus and buttons) that can be controlled using a cursor that is tied to where the user is pointing with their head or eyes/pupils. This allows further interaction with the received EAMS data, such as zooming in and out, and turning various visual elements on or off. Benefits of the embodiments described herein include: providing the user a better understanding of complex three-dimensional spatial relationships in the EAMS data, greater accuracy in positioning catheters or other medical tools, and reduced need for verbal communication with the EAMS technician, among other advantages.

The HMD provides the above benefits by receiving data from the EAMS and allowing the user to view the EAMS data and manipulate that view of the data. In conventional systems, the HMD user cannot affect the state or data of the EAMS itself. If the user wants to change the data on the EAMS itself (e.g., edit the shape of the patient anatomy), the user must verbally request that the technician perform the operations on her behalf. It is difficult and tedious to verbally convey complex spatial data using commands, and there is the risk that the technician will misunderstand some nuance in the user's communication.

The embodiments herein describe novel systems and methods that make use of 2-way communication between an HMD and EAMS and the benefits of doing so, e.g., compared to conventional systems using one-way communication from the EAMS to HMD.

In various embodiments, a system comprises a head-mounted display (HMD) worn by a user; a display monitor; and a processing system configured to: provide image data for display by the HMD based on data provided to the display monitor for a user interface displayed by the display monitor; receive, from the HMD, a gaze direction of the user; determine a position of a cursor displayed on the user interface based on the gaze direction of the HMD user; provide the position of the cursor to the display monitor to update display of the cursor on the display monitor; receive a user input from the HMD responsive to an action performed by the user; and provide user input information to the display monitor to update the user interface based on the user input and the position of the cursor.

In some embodiments, the processing system comprises a frame grabber configured to: receive the data provided to the display monitor for the user interface displayed by the display monitor.

In some embodiments, the processing system comprises: a first computing device; a second computing device configured to provide the image data for display by the HMD and receive the user input from the HMD; and a signal generator configured to transmit information associated with the user input to the first computing device, wherein the first computing device generates the user input information using the information associated with the user input.

In some embodiments, the signal generator transmits the information associated with the user input as a USB signal, and wherein the first computing device generates the user input information without using input from a mouse or keyboard.

In some embodiments, the second computing device receives the gaze direction of the user from the HMD, and wherein the first computing device provides the position of the cursor to the display monitor.

In some embodiments, the HMD is further configured to: display an augmented reality graphic; and responsive to determining that the user is interacting with the user interface, updating display of the augmented reality graphic to track the position of the cursor.

In some embodiments, the processing system is further configured to: determine that the action performed by the user is a selection of one of a plurality of user controls displayed in the user interface.

In some embodiments, the processing system is further configured to: provide registration information to a 3D anatomic information source.

In various embodiments, a method comprises: providing image data for display by a head-mounted display (HMD) worn by a user based on data provided to a display monitor for a user interface displayed by the display monitor; receiving, from the HMD, a gaze direction of the user; determining a position of a cursor displayed on the user interface based on the gaze direction of the HMD user; providing the position of the cursor to the display monitor to update display of the cursor on the display monitor; receiving a user input from the HMD responsive to an action performed by the user; and providing user input information to the display monitor to update the user interface based on the user input and the position of the cursor.

In some embodiments, the method further comprises receiving the data provided to the display monitor for the user interface displayed by the display monitor.

In some embodiments, the method further comprises transmitting, to a first computing device from a second computing device by a signal generator, information associated with the user input, wherein the first computing device generates the user input information using the information associated with the user input.

In some embodiments, the signal generator transmits the information associated with the user input as a USB signal, and wherein the first computing device generates the user input information without using input from a mouse or keyboard.

In some embodiments, the second computing device receives the gaze direction of the user from the HMD, and wherein the first computing device provides the position of the cursor to the display monitor.

In some embodiments, the method further comprises displaying, by the HMD, an augmented reality graphic; and responsive to determining that the user is interacting with the user interface, updating display of the augmented reality graphic to track the position of the cursor.

In some embodiments, the method further comprises determining that the action performed by the user is a selection of one of a plurality of user controls displayed in the user interface.

In some embodiments, the method further comprises providing registration information to a 3D anatomic information source.

In various embodiments, a non-transitory computer-readable storage medium stores instructions, the instructions when executed by one or more processors cause the one or more processors to perform any steps of the methods described herein.

In some embodiments, a processing system including an HMD sends live voice to the EAMS for an intercom with remote users, dictation of notes and procedure annotations, or voice control of EAMS functionality.

In some embodiments, a processing system including an HMD can remotely operate functionality that is otherwise provided to the EAMS technician via keyboard and mouse. Example functionality includes: having the EAMS start and stop collecting catheter-tissue contact points to generate or update the geometry of the patient anatomy; switching which catheter/tool is used for mapping; designating particular frames of an ultrasound or fluoroscopy images to be saved for later review; annotating features in the saved ultrasound or fluoroscopy images; changing the level-of-detail with which the EAMS generates patient anatomy geometry; specifying to the EAMS a sub-region of anatomy to be selected for operations such as cutting, trimming, deleting, smoothing, pushing inward or outward; commanding the EAMS to perform operations on selected sub-regions of the patient anatomy such as cutting, trimming, deleting, smoothing, pushing inward or outward; specifying to the EAMS how it should merge the currently anatomical geometry or electrical maps with others previously acquired, include those acquired from ultrasound, CT, and MRI images; commanding the EAMS turn on/off the collection of electrograms (EGMs); specifying to the EAMS which electrode on the catheter to highlight or turn on/off; specifying to the EAMS which type or style of visualization it should display on its 2D screen and which it should send to the HMD headset; specifying to the EAMS the thresholds and end points for the mapping from data to color; commanding the EAMS start and stop animated visualizations; specifying to the EAMS, to create marker points in space and/or time and attach notes or annotations to them for later editing or review (points can be relative to patient anatomy, catheter to tool tip positions, positions in ultrasound, CT, MRI, or X-ray images, or signal features in electrograms); specifying to the EAMS which anatomic samples, markers, tags or labels to select, edit or delete; commanding the EAMS take snapshot images or videos of the current EAMS screen, data, for later playback review or export to a patient medical record; commanding the EAMS to measure the distance between points and features in the anatomy (virtual calipers); commanding the EAMS to measure the timing differences between timestamps and features in the electrogram waveforms; commanding the EAMS to rewind, fast forward, pause and stop playback of previously recorded data; and commanding the EAMS to create annotations, such as lines and curves that are projected onto the 3D surface of the anatomy.

In some embodiments, the position and orientation of a user's head and/or eye gaze is sent by an HMD to the EAMS for the purpose of: displaying what the user is looking at (in the HMD) on the EAMS 2D display monitor; sharing what the user is looking at with remote EAMS and other users wearing HMDs; recording what the user is looking at in the recordings of medical procedure data; or moving computation tasks and workload from the HMD to the EAMS computing device (e.g., remote rendering with time warp or late stage reprojection, or resorting voxels and/or polygons by distance from the viewing user's position).

In some embodiments, a battery and/or temperature status of the HMD is sent to the EAMS and displayed by the EAMS in order to aid users in preparing for swapping to another HMD battery and troubleshooting.

In some embodiments, a processing system measures the throughput, jitter, latency, signal to noise ratio, and/or loss rate of a wireless network between the EAMS and HMD, so that the EAMS can reduce or increase the amount of data send to the EAMS, to manage the delays between when the EAMS sends the data and when the HMD displays it. The processing system can implement mesh decimation, progressive refinement of 2D or 3D images, or foveated rendering, with the highest-fidelity portion of the image being where the user is looking or where a catheter tip (or another part of a medical tool) is moving.

DETAILED DESCRIPTION

As disclosed herein, embodiments of a 2-way EAMS communication provide a user wearing an HMD greater and improved control of a user interface or other functionality.

In some embodiments, the HMD provides a user-interface (e.g., buttons and menus) that can be controlled hands-free by a user such as a physician and allow the physician to operate functions of the EAMS that would otherwise require the physician to make verbal requests to the EAMS technician.

Example commands that the HMD can send to the EAMS include: starting or stopping collection of contact points between a medical tool and tissue to generate or update information of the patient anatomy (e.g., geometry or shape); designating particular frames of an ultrasound or fluoroscopy images to be saved for later review; annotating features in the saved ultrasound or fluoroscopy images; switching which medical tool is used for mapping; turning on or off the collection of electrograms (EGMs); performing operations on selected sub-regions of the patient anatomy such as cutting, trimming, deleting, smoothing, pushing inward or outward; starting or stopping display of animated visualizations (e.g., BWI CARTO ripple map); taking snapshot images or videos of the current EAMS screen, data, for later playback review or export to a patient medical record; measuring a distance between points and features in the anatomy (e.g., virtual calipers); measuring timing differences between timestamps and features in the electrogram waveforms; and requesting rewind, fast forward, pause and stop playback of previously recorded data.

The HMD can send information to the EAMS for updating a display of the HMD. Example information include: a level-of-detail with which the EAMS generates patient anatomy geometry (e.g., changing to a more simplified or detailed level); a sub-region of anatomy to be selected for operations such as cutting, trimming, deleting, smoothing, pushing inward or outward; instructions to merge anatomical geometry or electrical maps with previously acquired data, e.g., acquired from ultrasound, CT, or MRI images; which electrode on the catheter to highlight or turn on/off; which type or style of visualization (e.g., map) should be displayed on a 2D display monitor or a HMD (e.g., in 3D); thresholds and end points for the mapping from data to color; creation of marker points in space or time, and associated notes or annotations for later editing or review (marker points can be relative to patient anatomy); catheter to tool tip positions; medical tool positions in ultrasound, CT, MRI, or X-ray images; signal features in electrograms; and which anatomic samples, markers, tags or labels to select, edit, or delete.

In various embodiments, functionality performed by the EAMS technician using a mouse and keyboard can also be controlled by the user wearing the HMD.

I. Electroanatomic Navigation and Mapping Systems (EAMS)

In an electrophysiology procedure, the operator-user and/or electrophysiologist-user may use a 2D display monitor, mouse, and keyboard to specify a 3-dimensional spatial relationship with 3 or 6 degrees of freedom (e.g., 3D position, direction and magnitude in 3D space, or 3D position and 3D orientation) with any number of supporting computer systems providing patient data. An example implementation is the EAMS. Any number of supporting systems may supply additional procedure data or instrument control adjacent to, or internal to EAMS data.

In some procedures, the user imports a 3D model of the patient anatomy (derived from a pre-operative CT, MRI, or ultrasound scan, or from a previously performed cardiac mapping procedure with an EAMS). The user then specifies how the imported 3D model spatially relates to the current intra-operative cardiac 3D model. Typically, the user must identify three or more corresponding 3D points on the surface of the models. The EAMS then computes the best-fit transformation between the two models. In other situations, the user uses the mouse to interactively apply any number of translations, rotations, and or scaling operations to models using a 2D display monitor, mouse, and/or keyboard.

In some procedures, a catheter is manipulated in part or whole robotically, via any number of mechanical cables, motors or magnetic or pneumatic actuators, internal or external to catheter. The user specifies the 3D trajectory vector, 3D path, and/or 3D target destination position. The robotic system then computes the appropriate actuations to steer and drive the catheter as the user has specified.

In some ablation systems, the direction in which the ablation energy is directed is electronically or mechanically steerable (e.g., high intensity focused ultrasound, phased-array RF antenna). The user specifies the 3D vector in which the ablation energy is directed from the emission point on the catheter.

In the above examples, because the EAMS user is using a 2D display monitor and a mouse with two degrees of motion, the user can only observe and adjust two degrees of freedom of the desired 3D spatial relationship at a time (which can have between three to six degrees of freedom). The user frequently cycles modes between (1) adjusting translation in 2D, (2) adjusting rotation in 2D, and (3) changing the viewing-orientation in 2D (i.e., pitch and yaw). The user would need to repeatedly iterate between these three modes to interpret, construct, adjust, and inspect the work-in-progress 3D spatial relationship until it is sufficiently similar to their intention. This manipulation requires practice and skill, and can be tedious, time consuming, and error prone.

II. System Overview

FIG. 1 illustrates an example system environment for a processing system 100 according to an embodiment. The system environment includes the processing system 100, one or more HMDs 110, one or more display monitors 120, and one or more input devices 130. The processing system 100 includes an EAMS computing device 102 (also referred to herein as "EAMS"), data computing device 104, frame grabber 106, and signal generator 108. In other embodiments, functionality of the processing system 100 may be performed by any number of devices. For example, instead of an EAMS computing device 102 separate from a data computing device 104, the processing system 100 includes one computing device (including memory and one or more processors) that performs the functionality of both the EAMS computing device 102 and data computing device 104, as well as the functionality of the frame grabber 106 and signal generator 108.

In some embodiments, the HMD 110 and EAMS computing device 102 functionality are performed on separate devices. One computing device is part of the EAMS and another computing device is part of the HMD 110. In other embodiments, the functionalities of the two computing devices are combined into a single computing device. In other embodiments, some of the functionality of the EAMS computing device 102 or HMD 110 is performed on remotely located server, which may also be part of the processing system 100.

The EAMS computing device 102 is communicatively coupled to the data computing device 104, e.g., over the Internet or another form of wireless or wired connection. The EAMS computing device 102 is communicatively coupled to the one or more input devices 130 such as a keyboard, mouse, or a 3D anatomic information source. The EAMS computing device 102 transmits information for display on the display monitor 120 (e.g., a computer monitor with a display such as an LCD, LED, OLED, plasma, or touchscreen display). The frame grabber 106 receives the information transmitted to the display monitor 120 and transmits it to the data computing device 104.

The data computing device 104 is communicatively coupled over a wireless or wired connection to the one or more HMDs 110. In conventional systems, the EAMS computing device 102 receives input from input devices such as a mouse or keyboard. The signal generator 108 can provide input to the EAMS computing device 102 that resembles input from a mouse or keyboard. The signal generator 108 generates an input signal (e.g., a USB signal) using information from the data computing device 104. An example use case is described below with respect to FIG. 2 and FIG. 3.

Figure 3:
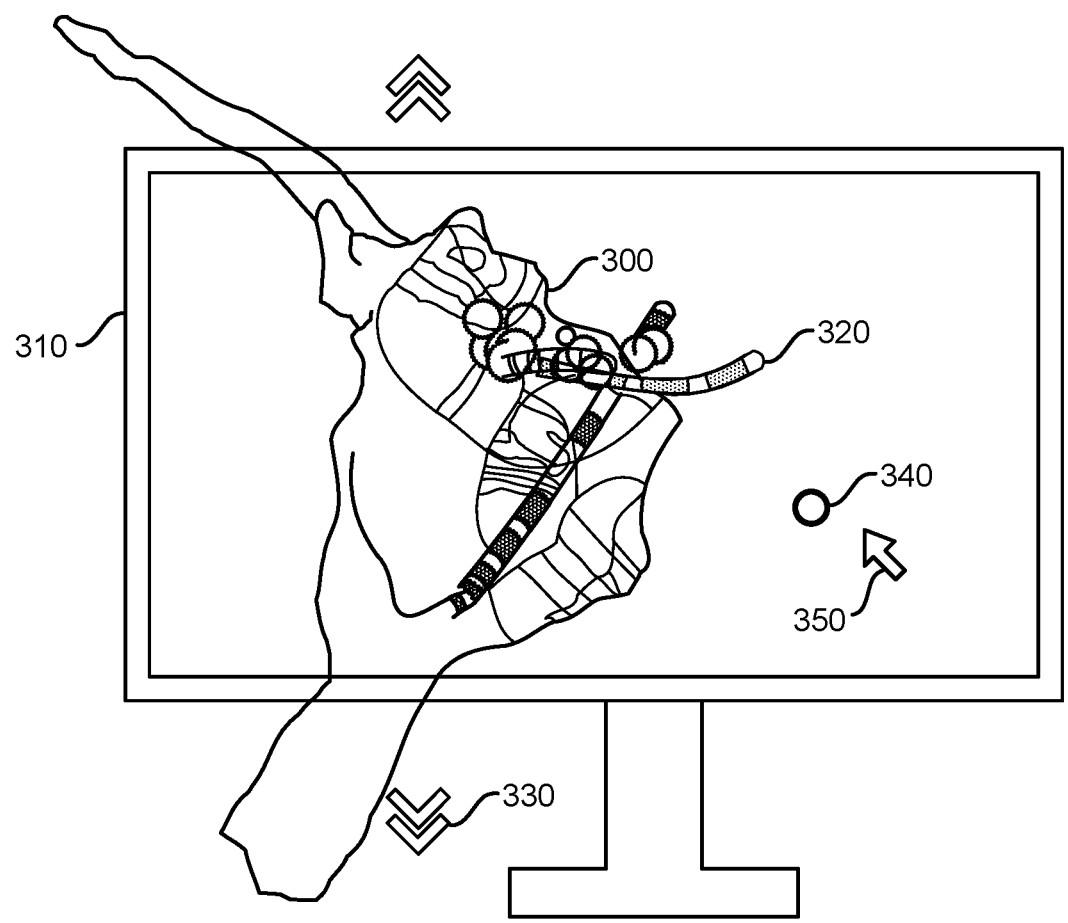
FIG. 3 illustrates an example user interface in an augmented reality environment according to an embodiment.

FIG. 2 is a flowchart of a process 200 for user control in an augmented reality environment according to an embodiment. FIG. 3 illustrates an example user interface in an augmented reality environment according to an embodiment. The processing system 100 performs the process 200, which may be used for a cardiac medical procedure, as illustrated in the example user interface shown in FIG. 3. In other embodiments, the process 200 applies to other types of medical procedures.

In step 210, the processing system 100 provides image data for display by the HMD 110 based on data provided to the display monitor 120 for a user interface displayed by the display monitor 120. In some embodiments, the data computing device 104 may perform step 210, and the EAMS computing device 102 provides the data to the display monitor 120 for the user interface. The data computing device 104 receives the data provided to the display monitor 120 via the frame grabber 106. As shown in FIG. 3, the HMD 110 displays an augmented reality graphic 300 that is a model of a patient's heart. The HMD 110 also displays other augmented reality graphics including a catheter 320 and user controls 330. Since the user is looking toward a display monitor 310, the HMD 110 displays the augmented reality graphic 300 and other graphics as holograms overlaid on the display monitor 310 from the user's point of view.

In step 220, the processing system 100 receives, from the HMD 110, a gaze direction of the user. The HMD 110 determines the gaze direction using sensor data captured by one or more sensors of the HMD 110. For example, the sensor data represents head direction or eye/pupil direction.

In step 230, the processing system 100 determines a position of a cursor displayed on the user interface based on the gaze direction of the HMD user. As shown in FIG. 3, the display monitor 310 displays a cursor 350 (e.g., a mouse cursor) on the user interface. Additionally, the HMD 110 displays a marker 340 to indicate the gaze direction of the HMD user. The processing system 100 may control the position of the cursor 350 based on the position of the marker 340. Specifically, in step 240, the processing system 100 provides the position of the cursor 350 to the display monitor 310 to update display of the cursor 350 on the display monitor 310. The processing system 100 updates the position of the cursor 350 to track the position of the marker 340, responsive to determining that the marker 340 is located within the area of the user interface displayed by the display monitor 310.

In step 250, the processing system 100 receives a user input from the HMD 110 responsive to an action performed by the user. The user input may be a hands-free input such as an eye gesture (e.g., wink or blink), head gesture (e.g., nod), or voice command. The processing system 100 can determine that the user input is an interaction with one or more user controls displayed in the user interface (e.g., a button, slider, menu, text input box).

In step 260, the processing system 100 provide user input information to the display monitor 310 to update the user interface based on the user input and the position of the cursor 350. As an example, the user performs the user input to start or stop a mapping or registration procedure. Instead of using a mouse or keyboard to interact with a user interface on the display monitor, the user can start or stop the procedure using hands-free input by directing the user's gaze to a virtual button (e.g., an augmented reality graphic) displayed by the HMD 110, or to a button on the display monitor (where the cursor tracks the user's gaze direction as indicated by the marker 340 shown in FIG. 3). Instead of a using a mouse click or pressing a keyboard key, the user provides a hands-free input such as a wink or blink to indicate a selection of a virtual button or a button on the display monitor. The signal generator 108 transmits information associated with the user input from the HMD 110 to the EAMS computing device 102, which processes the information as it would process input from a mouse or keyboard received via a USB signal.

As another use case, the user performs the user input to store a current 3D position of a catheter tip as a marker or sample point. The data computing device 104 continually computes the 2D coordinates—in the coordinate frame of the user interface of the display monitor 120—where the HMD gaze marker (e.g., marker 340 shown in FIG. 3) overlaps the user interface from the point-of-view of the user wearing the HMD. The data computing device 104 then generates USB mouse signals to update the cursor on the display monitor 120 to those coordinates such that the cursor appears to follow the HMD gaze marker. The user navigates the cursor to a pull-down menu of the user interface and selects the pull-down menu by winking or performing another type of touch-free action. The user can again use gaze direction and another action to select an option from the menu such as "store sample point."

In various embodiments, the EAMS and HMD can send data via a wired or wireless transmission, including USB, Ethernet, PCI, Bluetooth, Wi-Fi, ultra-wideband RF, optical link, and with topologies such as direct point-to-point, token ring, mesh, or via a central router. Examples of HMD devices include optical see-through augmented reality (AR) headsets (e.g., Microsoft HoloLens, ODG R-7, Magic Leap 1 and 2, or Nreal Light), camera-based see-through AR headsets (e.g., Oculus Quest, Varjo XR-3, or Lynx R1), fully opaque virtual reality (VR) headsets (e.g., HTC Vive and Valve Index), and other displays that can track the position or orientation of the user's head or gaze direction and display from the user's point-of-view.

Although the embodiments described herein reference a head-mounted display (HMD) 110, the disclosed systems and methods can also apply to non-head-mounted displays (e.g., fixed to the floor, ceiling, walls, table, or cart) that are monoscopic or stereoscopic (e.g., Looking Glass 8k Gen 2, Sony LMD-X310MT, or Steris VividImage 4k surgical display) and coupled with a head or eye tracker (e.g., Tobii Pro Fusion, Tobii Pro Spectrum, or Tobii Tracker 5). In some embodiments, the system combines a head-worn eye tracking apparatus (e.g., Tobii Pro Glasses 3, Pupil Labs Core, *Argus* Science, or ETVision) with a non-head-mounted display.

In various embodiments, a user interface that captures the user's commands for the EAMS can use any combination of sensing modalities including head-position and head-orientation, eye or pupil gaze direction, audio and voice input, hand or finger tracking, EEG (electroencephalography) or EMG (electromyography) sensors, facial gesture tracking (e.g., via camera, depth sensors, ultra-wideband RF, or short-range radar), tongue-switches, hand-held remote controllers, laser pointers, foot pedals, and buttons or joysticks mounted on a display or a proximal end of a catheters or medical tool.

Examples of EAMS systems include Johnson and Johnson Biosense Webster CARTO™, St. Jude Medical Ensite™ Velocity™, Medtronic LocaLisa™, Medtronic CardioInsight, Medtronic Affera.

In various embodiments, ultrasound images processed by the EAMS or HMD are acquired by Intracardiac, Transesophageal, External, 2D or 3D ultrasound transducers, with or without use of ultrasound contrast agents.

In various embodiments, the EAMS includes one or more navigation systems such as those used for procedures involving one or more of: heart, brain, sinuses, jaw, teeth, spine, knee, hip, lung, prostate, liver, kidney, vessels, prostate, pancreas, uterus, and abdomen.

The embodiments described herein can be used in conjunction with any number of catheters or other medical tools manipulated manually by a user's hands or assisted or controlled by motors or other mechanical actuators (e.g., robotically controlled or power-assisted, medical tools).

The disclosure herein typically refers to the user as a physician. However, the disclosed embodiments are also applicable to other types of users including veterinarians, nurses, trainees, instructors, technicians, engineers, administrators, and demonstrators, among other types of health care providers.

III. Head-Mounted Display (HMD)

In various embodiments, the HMD 110 comprises one or more displays and user input devices. In some embodiments, the user input is achieved through one or more microphones. In some embodiments, user input is achieved through observation of hand position and pose (e.g., using cameras or neuromuscular sensing). In some embodiments, user input is achieved through relative position and pose of the HMD (e.g., gaze or head position cursor). In some embodiments, user input is achieved through communicatively coupled sensors to provide any number of button input, hand position, pose, or neuromuscular signaling. In some embodiments, user input is achieved by tracking the position and pose of the eye (e.g., camera, neuromuscular sensing).

When viewed in a stereoscopic head-tracked mixed-reality HMD, the work-in-progress 3D spatial relationship can be much more salient to the user than when shown on a 2D display. Furthermore, the work-in-progress 3D spatial relationship can be adjusted simultaneously as it is inspected, without the user having to switch modes.

IV. 3D Registration

In an embodiment, a system comprising an HMD 110 worn by a user, a 2D display monitor 120, and a processing system 100 configured to provide any number of 3D anatomic information and responsive to a transformation between 3D anatomic coordinate systems, enables the user to intuitively specify, update, and/or observe the registration of the 3D anatomic information in a combined coordinate system.

In some embodiments, a 3D anatomic information (e.g., registration information) is intraoperatively generated and transmitted by an EAMS and is transmitted to the processing system 100 for registration with another 3D anatomic information source (e.g., an input device 130). In other embodiments, the 3D anatomic information is transmitted through a Picture Archiving and Communication System (PACS) for registration. In other embodiments, the 3D anatomic information is generated by the processing system 100 by combining 3D information from one source (e.g., catheter position) with another source (e.g., electrogram recording system, ultrasound).

In some embodiments, the processing system 100 transmits registration information to the 3D anatomic information source through the emulation of inputs native to the 3D anatomic information source to aid in registration (e.g., a sequence of any number of keyboard or mouse operations). These operations would apply the normal registration operations of the existing 3D anatomic information source. In other embodiments, the registration information is communicated from the processing system 100 to the 3D anatomic information source by providing a set of corresponding points from the source information source to the destination information source. In some embodiments, the registration information is communicated from the processing system 100 to the 3D anatomic information source by providing a function to transform any input position and/or pose from one anatomic information source to the other anatomic information source. In some embodiments, the transformation is solely contained and displayed within the processing system 100, and information is translated within the processing system 100, and communications between anatomic information sources is communicated within each systems native coordinate system.

V. Catheter Manipulation

In an embodiment, a system comprising an HMD 110 worn by a user and a processing system 100 configured to receive at least one 3D anatomic information source, and communicate with at least one catheter manipulator, enables the user to intuitively specify, update, and/or observe the manipulation of any number of catheters.

In some embodiments, the user specifies a target 3D position for the catheter manipulator. In some embodiments, the user specifies a sequence of target 3D positions for the catheter manipulator to create a target path. In some embodiments, the user specifies 3D positions, and target poses for the HMD manipulator to specify both position and orientation of the catheter at any number of positions. In some embodiments, the processing system 100 communicates with the manipulator through the EAMS. In some embodiments, the processing system 100 communicates with the catheter manipulator independent of the EAMS.

VI. Steerable Catheter

In an embodiment, a system comprising an HMD 110 worn by a user and a processing system 100 configured to receive at least one 3D anatomic information source, and communicate with at least one configurable catheter ablation system, enables the user to intuitively specify, update, and/or observe the 3D parameters of a catheter ablation system. In some embodiments, the user specifies and observes directional detection parameters (e.g., electrode selection in an array, ultrasound). In some embodiments, the user specifies ablation direction parameters (e.g., electrode in an array, phase, laser direction). In some embodiments the processing system 100 communicates with the catheter ablation system through the EAMS. In some embodiments, the processing system 100 communicates with the catheter ablation system independent of the EAMS.

VII. User Input

In some embodiments, user input from the HMD 110 is achieved by detecting and transmitting any number of click operations to indicate a discrete event (e.g., start, stop). In some embodiments, these click operations are achieved hands-free and touch-free, by holding the user head pose within a movement tolerance for a dwell period of time (Gaze-Dwell). In other embodiments, these click operations are achieved through a hand-held controller communicating with the HMD 110 and/or processing system 100. In some embodiments, these operations are detected through processing of voice commands using a dictionary, or derived intent using any number of voice intent detection operations. In some embodiments, these operations are detected through physical gestures including facial expressions, hand poses or movements, eye poses or movements, etc. Physical gestures may be detected and classified as an operation by observing neuromuscular signals. Additionally, physical gestures may be detected by processing sequences of image data from 2D sensors, including electro-optical, or infrared (IR). In some embodiments, these discrete inputs are segmented into a range of variable inputs to provide a range of intermediate values (e.g., [0-10]).

In various embodiments, 2D user input from an HMD 110 is achieved by detecting and transmitting an absolute or relative 2D position change. In some embodiments, this 2D information is calculated by processing the position of the HMD gaze cursor relative to the extent of a virtual or physical display. In some embodiments, coordinates may be transformed between virtual and physical displays to facilitate manipulation by the user wearing the HMD 110, e.g., electrograms may be increased in virtual scale to provide greater precision with hands free control as in EGM Annotation.

In various embodiments, 3D user input from an HMD 110 is achieved by detecting and transmitting an absolute or relative 3D position change. In some embodiments, this 3D information is calculated by processing 3D position change of the user wearing the HMD 110. In some embodiments, 3D information is calculated by processing the position of a single hand input of the user. In some embodiments, 3D information is calculated through processing of the difference between two hand inputs of the user. Hand input may be achieved through camera-based hand tracking or a hand-held or hand-worn controller input. In various embodiments, 3D position and pose information is available in addition to 3D position. The processing system 100 can calculate this information from a single input, e.g., the position and pose of a single hand, or from a combination of inputs, e.g., the position of one hand, and the relative position of another hand forming the basis of a pose vector.

VIII. Multiple User Use Cases

The above embodiments may also be used by multiple users simultaneously or sequentially, to allow the collection of users to collaborate in specifying the 3D spatial relationship. For example, one user wearing an HMD may use the hand-held-controller to make the large gross adjustments to the work-in-progress 3D spatial relationship and then another user wearing another HMD (who may have sterile hands) may make small precise refinements to the work-in-progress 3D spatial relationship. Similarly, the EAMS-operator, who is sitting at a desk, may assist an HMD-wearing user by making the large gross adjustments to the work-in-progress 3D spatial relationship using a mouse and keyboard while the HMD-wearing user, who is standing next to the patient, may make smaller precise refinements to the work-in-progress 3D spatial relationship.

In some embodiments, when multiple users are given the ability to specify the 3D spatial relationship, it may be easier for the users to understand how to operate the processing system 100 if the system enforces that only a single user is allowed to virtually grasp the pre-operative model, 3D trajectory, 3D direction and magnitude, or 3D point at a time. Depending on if the processing system 100 consists of a single or multiple processing units, a traditional shared-memory mutex or distrusted mutex algorithm (e.g., Suzuki—Kasami algorithm, Ricart— Agrawala algorithm) may be used to lock-out users from grasping the virtually grasp the pre-operative model, 3D trajectory, 3D direction and magnitude, or 3D point until the current owner has released it.

In some embodiments, the HMD 110 must transmit the 3D spatial relationship back to the EAMS computing device 102. In some embodiments, the HMD 110 keeps the work-in-progress 3D spatial relationship private to itself until a user has signaled that they are finished specifying it, and then HMD 110 transmits the completed 3D spatial relationship to the EAMS computing device 102. In other embodiments, the HMD 110 continually or periodically transmits the work-in-progress 3D spatial relationship to the EAMS computing device 102 while the user is still manipulating and refining it.

IX. EAMS API

In some embodiments, an EAMS API outputs the positions, orientations and shapes of the catheters, a geometrical and visual description of the 3D cardiac model, and/or the waveforms of signals sensed by the electrodes on the catheters. In addition to outputting these elements over an API, the EAMS typically displays these elements on its own 2D display. The HMD 110 can use the data from the EAMS API to reconstruct the appearance of portions of the EAMS display monitor 120. The allows the HMD 110 to perform a pattern match between the live video acquired by a camera of the HMD 110 (with a view of the EAMS 2D display monitor) and the reconstructed EAMS elements instead of desktop video captured by a frame grabber 106. This has the benefit of needing fewer hardware components.

In some embodiments, the waveforms of signals captured by the catheter electrodes may not only appear on the EAMS display monitor 120 but may also be digitized by a device external to the EAMS (e.g., GE Cardiolab). This external digitizer device (an input device 130) may send the waveforms of the signals via the processing system 100 to the HMD 110 using a digitizer API that is independent of the EAMS API.

In some embodiments, the EAMS computing device 102 assists detection by the HMD 110 of the EAMS video captured in the camera video of the HMD 110, by adding one or more additional 2D graphic elements to the EAMS screen shown by display monitor 120, and sending a description of the additional 2D graphic elements over the EAMS API. The additional elements are designed to be more easily recognizable in the HMD's camera video than typical EAMS desktop video (by being high-contrast and having unique features). Examples of additional 2D graphic elements include Aruco fiducials, QR codes, April tags, and 2D barcodes.

X. Using 2-Way EAMS Communication for Improving Collaboration with Users Who are Viewing the 2D EAMS Display Because conventional EAMS systems without an HMD use a 2D display, the EAMS technician will slightly rotate the view back and forth (wobble) around a point of interest, to give the viewers a better understanding of the displayed 3D spatial relationships. As an example, this is commonly done when the physician is using the catheter tip to apply radio frequency (RF) energy to a specific point in the patient tissues and must carefully control the tip's position in the anatomy. There is less need for the EAMS technician to wobble the view in the HMD because the HMD is stereoscopic and thus the view naturally wobbles with the user's inherent postural sway while standing.

In some embodiments, the people looking at the 2D EAMS system screen on a display monitor 120 (e.g., the EAMS technician and other people in the room not wearing the HMD 110) can be given more awareness of what a user wearing the HMD 110 is doing. The processing system 100 receives from the HMD 110 the point-of-interest that the user is looking at and cause the EAMS view to wobble about that point on the EAMS 2D display. In some embodiments, the EAMS view is centered on and follows whatever point the HMD user is looking at, to provide those people who are observing the medical procedure more context regarding what the physician is doing, and the patterns in which they scan the information on the displays and medical images. In other embodiments, the user's head direction (based on head position and orientation) or gaze direction are represented on the EAMS 2D display as a laser-pointer or cursor. If the EAMS technician is using the cursor to highlight a location on the 2D EAMS display, the cursor can be shown by the HMD 110 (e.g., as a point on the geometry or a 3D ray).

In some embodiments, the EAMS display shows the battery or heat status of the HMD 110, so that a physician's assistants can anticipate when the HMD 110 will need to be swapped with another, or having its battery replaced. Other notifications, warnings, or errors displayed by the HMD 110 can be mirrored on the EAMS display on a display monitor 120, so that the physician's assistants can aid in addressing those messages.

In various embodiments, 2-way communication between the EAMS computing device 102 and the HMD 110 improves communication with users who are remotely located, e.g., not in the same procedure room as the user wearing the HMD 110.

In some embodiments, the data that flows from the HMD 110 to the EAMS computing device 102 is then routed (by the EAMS) to remote systems and users. This allows remote users to better understand what the HMD user is doing and to provide supervision, assistance, feedback, or ask questions from remote locations. The data sent from the HMD 110 to the EAMS includes, e.g., audio of the HMD user's voice, allowing for remote-voice control, note-taking, and intercom between remotely located users. In some embodiments, the EAMS technician themselves are located remote from the procedure room. In some embodiments, the HMD 110 may receive and send data to multiple EAMS simultaneously.

XI. Using 2-Way EAMS Communication for Reducing Computational Demands on the HMD Example design factors of an HMD 110 include weight, size, heat dissipation, comfort, aesthetics, and battery life. Due to design trade-offs such as reducing weight for user comfort, the HMD 110 may have less computing power compared to the EAMS computing device 102, for example, a high-performance computer workstation that does not need to be lightweight. It is advantageous to reduce computing power required by the HMD 110 (e.g., by implementing more efficient algorithms) to further reduce weight, cost, and heat, and improve comfort and aesthetics.

In various embodiments, the HMD 110 sends information to the EAMS including the position and orientation of the HMD 110, or the user's gaze direction. The HMD 110 or EAMS can determine a point of view of the HMD 110 (representing the user's point of view) using any combination of the HMD position, HMD orientation, and user's gaze direction. Based on the point of view, the EAMS can pre-process data to reduce the computational resources required by the HMD 110 to generate a resulting graphics (e.g., images or video) on the HMD 110. In various embodiments, the EAMS sends imaged patient anatomy data as a 3D mesh of triangles or as collection of 3D voxels (e.g., a 3D texture) to the HMD 110 (e.g., via the data computing device 104). The HMD 110 sorts these triangles or voxels such that those farther away in spatial distance from the user are rendered first, and those closest to the user are rendered last, to correctly simulate occlusion and transparency (known to those skilled in the art as the painter's algorithm).

In some embodiments, the EAMS sorts the triangles and voxels before sending the sorted triangles and voxels to the HMD 110. Since the user may have physically moved while the EAMS performs the sorting (e.g., a duration less than a second), the point of view of the HMD 110 may also have changed during this duration. The user's movement during the EAMS sorting is typically a slight movement rather than a significant change in orientation or position, so minimal artifacts occur when the HMD 110 renders the sorted triangles and voxels. In situations when the point of view changes to a greater extent during EAMS sorting, the HMD 110 can perform an additional sorting operation to account for the user's movement and mitigate any artifacts. Performing the additional sorting operation requires fewer computational resources than a full sort by the HMD 110 because the collection of triangles and voxels were still pre-sorted by the EAMS, which reduces the sorting required by the HMD 110.

In some embodiments, the EAMS renders imaging data and sends the rendered video image frames to the HMD 110 instead of sending anatomy shapes and positions of a catheter or medical tool (known to those skilled in the art as the remote rendering). The video image frames include the color of pixels and the depth from the user's eye. This enables the HMD 110 to adjust the received frames to account for minor changes in the HMD point of view that result from the user's movement. As previously described, such user movement during image processing may cause artifacts in the rendered images. This process of adjusting the outdated images is known to those skilled in the art as the late stage reprojection or time warp.

XII. Using 2-Way EAMS Communication for Adapting to Wireless Network Speed

In various embodiments, the HMD 110 worn by a user receives data from the EAMS computing device 102 via a wireless network (e.g., the Internet, WIFI, Ultrawide Band, or Bluetooth). The capacity of the wireless network is limited, and can vary over time based on factors such as the number of other wireless devices in the vicinity, the distance between the EAMS and the HMD 110, the arrangement of other equipment, walls, and people in the procedure room, etc. The EAMS data can be delayed by network conditions, causing the positions of catheters or medical tools displayed by the HMD 110 to fall behind their actual locations in the patient, which in turn may cause the physician to have more difficulty in steering the catheter to an intended target.

There is generally a trade-off between the level-of-detail or fidelity in a computer-generated image, and the amount of data required to be transmitted to reproduce that image in HMD 110. In some embodiments, the HMD 110 can measure the network reception strength, signal to noise level, latency, or throughput, and feedback this data to the EAMS. Based on this feedback, the EAMS can adjust the level-of-detail in the data sent to the HMD 110, forming a closed-loop control system. For example, when the network's throughput is less than the rate of data that the EAMS is sending, the EAMS can throttle the data being sent in such a way that it is more likely to reach the HMD 110 in a timely manner.

In some embodiments, the EAMS computing device 102 sends (e.g., via the data computing device 104) the shape of the patient anatomy as a 3D mesh of triangles or as collection of 3D voxels to the HMD 110. The EAMS may reduce the number of triangles, the precision in the positions of the vertexes of the triangles, the resolution of the 3D texture, or any combination thereof. These actions result in a less detailed image of the anatomy displayed by the HMD 110. In some embodiments, the EAMS further reduces detail in regions of anatomy that are further away in distance from the point of view of the HMD 110 (known to those skilled in the art as foveated rendering) or further away in distance from a position of a medical tool such as the distal tip of a catheter.

In some embodiments, when a catheter is moving slowly, the EAMS sends data to the HMD 110 at a higher level of detail because the transmission time is not a limiting factor. In contrast, when a catheter is moving quickly, the EAMS sends data to the HMD 110 at a lower level of detail, but at a faster rate of transmission to ensure that the HMD 110 is updated in a timely manner to reflect the catheter movement.

In some embodiments, the EAMS reduces the level of detail in the positions and shapes of a catheter or medical tool when network speed is diminished. For example, the EAMS reduces precision in positions or reduces the number of control points in splines. The EAMS allocates more detail or bandwidth to the catheters that are moving quickly (e.g., above a threshold rate of change or relative to movement of other catheters) or that have distal tips closer to the HMD point of gaze. The EAMS can determine a greater image update rate of catheters moving more quickly (e.g., movement by user manipulation or control by a system). The EAMS can determine a greater image update rate of catheters located closer to the HMD point of gaze.

XIII. Additional Configurations

The disclosed embodiments are not mutually exclusive. They may be combined into an embodiment to provide a user with multiple options during the medical procedure. For example, a user may start specifying a 3D spatial relationship according to a hand-held-controller embodiment and then then put down the hand-held-controller and continue to refine the 3D spatial relationship according to a hands-free embodiment.

The foregoing description of the embodiments of the disclosure has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules can be embodied in software, firmware, hardware, or any combinations thereof.

Any of the steps, operations, or processes described herein can be performed or implemented with one or more hardware or software modules, alone or in combination with other devices. In some embodiments, a software module is implemented with a computer program product including a non-transitory computer-readable storage medium containing computer program code, which can be executed by a computer processor for performing any or all of the steps, operations, or processes described.

Embodiments can also relate to a product that is produced by a computing process described herein. Such a product can include information resulting from a computing process, where the information is stored on a non-transitory, tangible computer readable storage medium and can include any embodiment of a computer program product or other data combination described herein.

Finally, the language used in the specification has been principally selected for readability and instructional purposes, and it cannot have been selected to delineate or circumscribe the inventive subject matter. It is therefore intended that the scope of the invention be limited not by this detailed description, but rather by any claims that issue on an application based hereon. Accordingly, the disclosure of the embodiments herein is intended to be illustrative, but not limiting, of the scope of the invention, which is set forth in the following claims.

What is claimed is:

1. A system comprising:
  a head-mounted display (HMD) worn by a user, wherein the HMD is configured to display an augmented reality graphic;
  a display monitor; and
  a processing system configured to:
    provide image data for display by the HMD based on data provided to the display monitor for a user interface displayed by the display monitor,
      wherein the image data includes a collection of 3D voxels;
    receive, from the HMD, a gaze direction of the user;
    determine a position of a cursor displayed on the user interface based on the gaze direction of the user;

provide the position of the cursor to the display monitor to update display of the cursor on the display monitor;
pre-process the image data based on the gaze direction of the user by sorting the collection of 3D voxels; and
provide the pre-processed image data to the HMD, wherein the HMD further processes the pre-processed image data by performing an additional sort of a subset of the sorted collection of 3D voxels to account for change in the gaze direction of the user and to display the augmented reality graphic.

2. The system of claim 1, wherein the processing system comprises a frame grabber configured to:
receive the data provided to the display monitor for the user interface displayed by the display monitor.

3. The system of claim 1, wherein the processing system comprises:
a first computing device;
a second computing device configured to provide the image data for display by the HMD and receive the user input from the HMD; and
a signal generator configured to transmit information associated with the user input to the first computing device, wherein the first computing device generates the user input information using the information associated with the user input, wherein the user input information is provided to the display monitor to update the user interface based on the user input and the position of the cursor.

4. The system of claim 3, wherein the signal generator transmits the information associated with the user input as a USB signal, and wherein the first computing device generates the user input information without using input from a mouse or keyboard.

5. The system of claim 3, wherein the second computing device receives the gaze direction of the user from the HMD, and wherein the first computing device provides the position of the cursor to the display monitor.

6. The system of claim 1, wherein the processing system is further configured to:
determine a level of detail for the image data; and
transmit the image data at the level of detail to the HMD.

7. The system of claim 1, wherein the processing system is further configured to:
receive a user input from the HMD responsive to an action performed by the user; and
determine that the action performed by the user is a selection of one of a plurality of user controls displayed in the user interface.

8. The system of claim 1, wherein the processing system is further configured to:
provide registration information to a 3D anatomic information source.

9. A method comprising:
providing image data for display by a head-mounted display (HMD) worn by a user based on data provided to a display monitor for a user interface displayed by the display monitor, wherein the HMD is configured to display an augmented reality graphic, wherein the image data includes a collection of 3D voxels;
receiving, from the HMD, a gaze direction of the user;
determining a position of a cursor displayed on the user interface based on the gaze direction of the user;
providing the position of the cursor to the display monitor to update display of the cursor on the display monitor;
pre-processing the image data based on the gaze direction of the user by sorting the collection of 3D voxels; and
providing the pre-processed image data to the HMD, wherein the HMD further processes the pre-processed image data by performing an additional sort of a subset of the sorted collection of 3D voxels to account for change in the gaze direction of the user and to display the augmented radlity graphic.

10. The method of claim 9, further comprising:
receiving the data provided to the display monitor for the user interface displayed by the display monitor.

11. The method of claim 9, further comprising:
transmitting, to a first computing device from a second computing device by a signal generator, information associated with the user input, wherein the first computing device generates the user input information using the information associated with the user input, wherein the user input information is provided to the display monitor to update the user interface based on the user input and the position of the cursor.

12. The method of claim 11, wherein the signal generator transmits the information associated with the user input as a USB signal, and wherein the first computing device generates the user input information without using input from a mouse or keyboard.

13. The method of claim 11, wherein the second computing device receives the gaze direction of the user from the HMD, and wherein the first computing device provides the position of the cursor to the display monitor.

14. The method of claim 9, further comprising:
determining a level of detail for the image data; and
transmitting the image data at the level of detail to the HMD.

15. The method of claim 9, further comprising:
receiving a user input from the HMD responsive to an action performed by the user; and
determining that the action performed by the user is a selection of one of a plurality of user controls displayed in the user interface.

16. The method of claim 9, further comprising:
providing registration information to a 3D anatomic information source.

17. A non-transitory computer-readable storage medium storing instructions, the instructions when executed by one or more processors cause the one or more processors to:
provide image data for display by a head-mounted display (HMD) worn by a user based on data provided to a display monitor for a user interface displayed by the display monitor, wherein the HMD is configured to display an augmented reality graphic;
receive, from the HMD, a gaze direction of the user;
determine a position of a cursor displayed on the user interface based on the gaze direction of the user;
provide the position of the cursor to the display monitor to update display of the cursor on the display monitor;
determine a level of detail for the image data; and
transmit the image data at the level of detail to the HMD.

18. The non-transitory computer-readable storage medium of claim 17, storing further instructions that when executed by the one or more processors cause the one or more processors to:
transmit, to a first computing device from a second computing device by a signal generator, information associated with the user input, wherein the first computing device generates the user input information using the information associated with the user input, wherein the user input information is provided to the display monitor to update the user interface based on the user input and the position of the cursor.

19. The non-transitory computer-readable storage medium of claim 17, storing further instructions that when executed by the one or more processors cause the one or more processors to:
determine a speed of movement of an instrument for a medical procedure, wherein the level of detail for the image data is determined based on the speed of movement.

20. The non-transitory computer-readable storage medium of claim 17, storing further instructions that when executed by the one or more processors cause the one or more processors to:
determine a network speed of a wireless connection to the HMD, wherein the level of detail for the image data is determined based on the network speed, and wherein the image data is transmitted over the wireless connection to the HMD.

* * * * *